United States Patent [19]

Miyagi

[11] Patent Number: 5,601,549
[45] Date of Patent: Feb. 11, 1997

[54] MEDICAL OBSERVING INSTRUMENT

[75] Inventor: Kunihiko Miyagi, Saitama-ken, Japan

[73] Assignee: Machida Endoscope Co., Ltd., Tokyo, Japan

[21] Appl. No.: 552,284

[22] Filed: Nov. 2, 1995

[30] Foreign Application Priority Data

Nov. 17, 1994 [JP] Japan .................................. 6-308220

[51] Int. Cl.$^6$ ...................................... A61B 17/36
[52] U.S. Cl. ............................................ 606/4
[58] Field of Search ........................ 606/4, 10, 11, 606/12, 14, 15, 16, 17, 18

[56] References Cited

U.S. PATENT DOCUMENTS

| | | | |
|---|---|---|---|
| 3,796,220 | 3/1974 | Bredemeier | 606/18 |
| 4,877,016 | 10/1989 | Kantor et al. | 128/6 |
| 5,026,368 | 6/1991 | Adair | 606/15 |
| 5,041,108 | 8/1991 | Fox et al. | 606/15 |
| 5,179,938 | 1/1993 | Lonky | 606/3 |

FOREIGN PATENT DOCUMENTS

| | | |
|---|---|---|
| 0418109 | 3/1991 | European Pat. Off. . |
| 4320579 | 12/1993 | Germany . |
| 4422522 | 2/1995 | Germany . |
| 2-104329 | 4/1990 | Japan . |
| 2-191424 | 7/1990 | Japan . |
| 5-215970 | 8/1993 | Japan . |

OTHER PUBLICATIONS

Shoten K. K., Nagai, "Medical Optical Instrument", issued Apr. 1, 1971.

Primary Examiner—Angela D. Sykes
Assistant Examiner—Sonya Harris-Ogugua
Attorney, Agent, or Firm—Fish & Richardson P.C.

[57] ABSTRACT

An enlarging optical system having an objective lens and an ocular lens is received in a body of a microscope. A beam splitter is received in the body on an optical path of the enlarging optical system. This beam splitter is disposed between the objective lens and the ocular lens. A monitor television is also received in the body. An image obtained by an endoscope is displayed in this monitor television. The image displayed in the monitor television is reflected by the beam splitter toward the ocular lens.

12 Claims, 3 Drawing Sheets

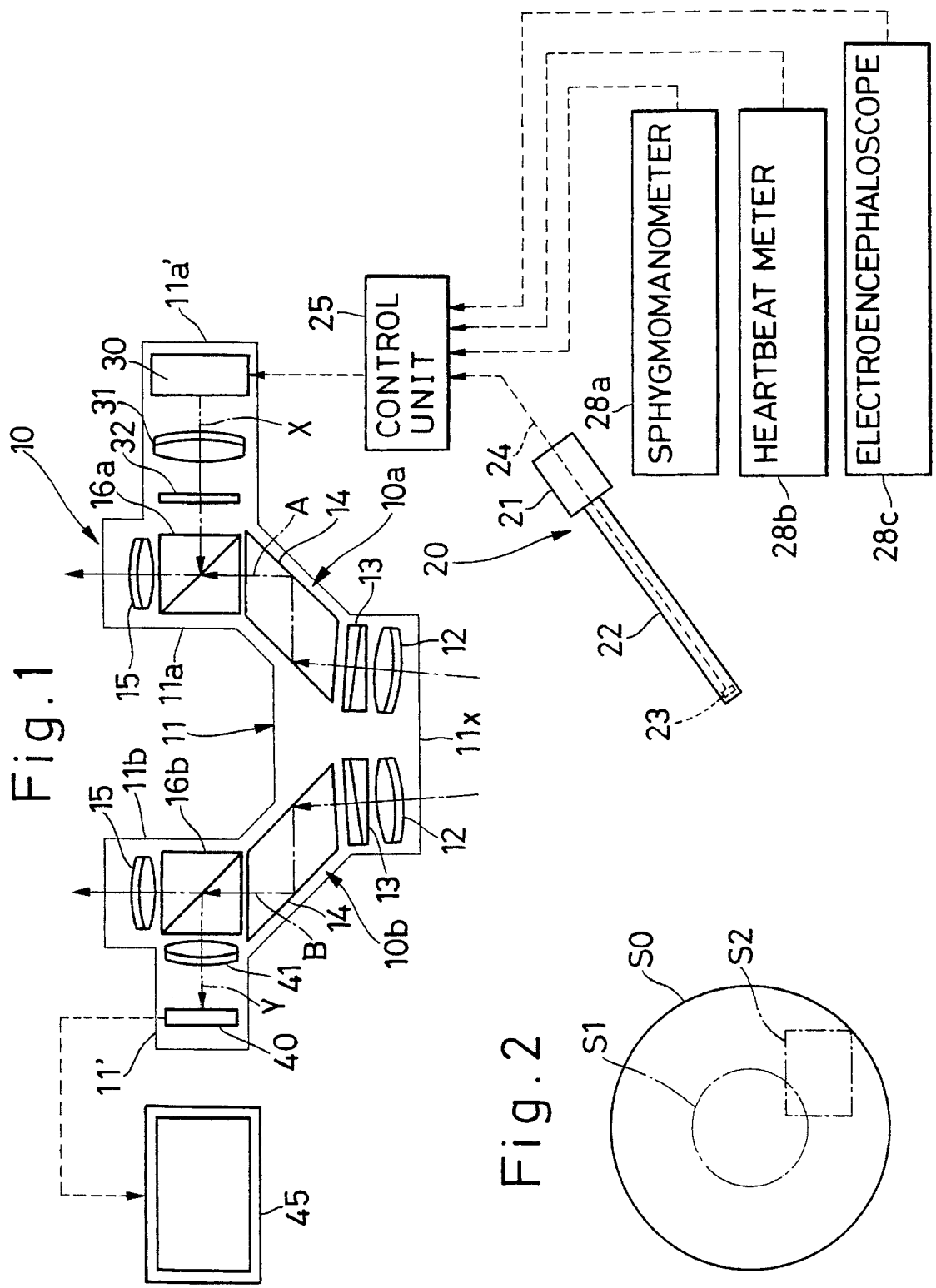

MEDICAL OBSERVING INSTRUMENT

BACKGROUND OF THE INVENTION

This invention relates to a medical observing instrument for the use in a micro-operation with respect to the ear, eye, brain, etc. of a patient.

Lately, as disclosed in "MEDICAL OPTICAL INSTRUMENT" issued Apr. 1, 1971 by Nagai Shoten K. K., a microscope is used in a micro-operation with respect to the ear, eye, brain, etc. of a patient. The operator performs an operation while observing an enlarged image of a diseased part of the patient and with the eyes placed coincident with a pair of ocular lens of a microscope. The microscope is usually supported in its suspending or hanging-down state. Therefore, the operator can see the diseased part only from a limited range of angles. However, it sometimes occurs that the operator is required to observe the diseased part from different angles during operation. For this purpose, the operator or an assistant to the operator manually holds an endoscope with an image sensor and brings it toward the diseased part. An image obtained by the endoscope is displayed in a monitor television which is located in place away from the microscope.

In this conventional method, however, it is necessary for the operator to temporarily remove the eyes from ocular portions of the microscope in order to observe the monitor television. Since this requires the operator to greatly change the sight line, a smooth operation is interrupted.

SUMMARY OF THE INVENTION

It is, therefore, an object of the present invention to provide a medical observing instrument in which an operator can observe a diseased part obtained through an endoscope, without greatly changing the sight line from a state in which the operator observes the diseased part through a microscope.

According to the present invention, there is provided a medical observing instrument comprising:

(a) a microscope having a body and an enlarging optical system received in the body, the enlarging optical system including an objective lens and an ocular lens;

(b) an endoscope; and (c) image display means for displaying an image obtained by the endoscope, the image display means being disposed at the body of the microscope.

BRIEF DESCRIPTION OF THE DRAWING

FIG. 1 is a schematic view showing one embodiment of a medical observing instrument according to the present invention;

FIG. 2 is an illustration of a view field of a microscope and a view field of a monitor television in one of a pair of ocular portions of the microscope of the medical observing instrument;

DETAILED DESCRIPTION OF THE EMBODIMENTS

Figure 3:
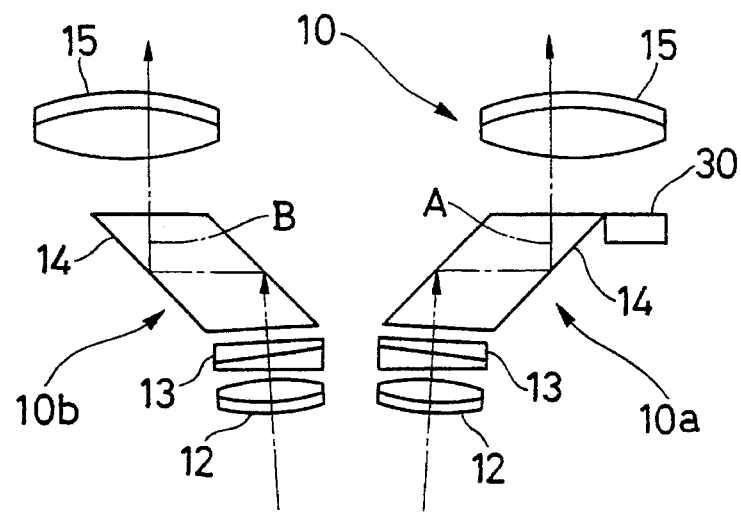
FIG. 3 is a schematic view showing an important portion of another embodiment.

One embodiment of the present invention will now be described with reference to FIGS. 1 and 2. As shown in FIG. 1, a medical observing instrument comprises, as principal component elements, a microscope 10 and an endoscope 20.

The microscope 10 has a binocular-like body 11. This body 11 has a base portion 11x, and a pair of ocular portions 11a, 11b projecting from a rear surface of the base portion 11x. The body 11 is supported by a hanging device, not shown, such that the position of body 11 can be adjusted. A pair of enlarging optical systems 10a, 10b are received in the body 11. Each of the enlarging optical systems 10a, 10b includes, as in the case with the conventional microscope, an objective lens 12, prisms 13, 14, and ocular lens 15. The microscope 10 includes an optical system (not shown) for emitting an illumination light to a diseased part of a patient.

In this embodiment, beam splitters 16a, 16b are disposed respectively on optical paths A, B of the enlarging optical systems 10a, 10b between the prism 14 and the ocular lens 15. The ocular lens 15 and the beam splitter 16a of the enlarging optical system 10a are received in the ocular portion 11a. On the other hand, the ocular lens 15 and the beam splitter 16b of the enlarging optical system 10b are received in the other ocular portion 11b of the body 11.

The body 11 has auxiliary receiving portions 11a', 11b' projecting at right angles respectively from the ocular portions 11a, 11b. In the auxiliary receiving portion 11a', a micro-monitor television 30 (image display means), a lens 31 and a shutter 32 are arranged in this order toward the beam splitter 16a. An optical path X where the monitor television 30, the lens 31 and the shutter 32 are arranged is intersected with the optical path A of the enlarging optical system 10a at the beam splitter 16a. The angle of intersection is somewhat smaller or larger than 90 degrees. A screen of the monitor television 30 is intersected at right angles with the optical path X.

An image obtained through the endoscope 20 is displayed in the monitor television 30. More specifically, this endoscope 20 has a body 21 and a hard tube 22 extending from the body 21. The tube 22 has an illuminating window and an observing window (both not shown) formed in a distal end of the tube 22. An illumination light is supplied from the illuminating window through a bundle of optical fibers extending through the body 21 and the tube 22. An image sensor 23 such as a CCD or the like is faced with the observing window through a lens. This image sensor 23 is connected to a control unit 25 (control means) through signal wires 24. This control unit 25 is operated to control the image sensor 23, prepares a television signal based on a picture signal from the image sensor 23 and sends it to the monitor television 30.

Various means for detecting the conditions of the patient such as a sphygmomanometer 28a, a heartbeat meter 28b, an electroencephaloscope 28c and the like are connected to the control unit 25. The control unit 25 prepares a picture signal indicative of a numeric figure based on blood pressure data obtainable from the sphygmomanometer 28a, prepares a picture signal representative of a numeric figure and a waveform based on heartbeat data obtainable from the heartbeat meter 28b, prepares a picture signal indicative of a waveform based on brain wave data obtainable from the electroencephaloscope 28c, combines them with the picture signal from the image sensor, and sends them to the monitor television 30. As a consequence, the numerical figures and waveforms are displayed in a certain area, for example, a right and down corner area of the screen of the monitor television 30. The circuit portion of the control unit 25 may be built in the monitor television 30.

In the other auxiliary receiving portion 11b', an image sensor 40 such as a CCD or the like and a lens 41 are arranged in this order toward the beam splitter 16b. An optical axis Y where the image sensor 40 and the lens 41 are arranged is intersected at 90 degrees with the optical path B of the enlarging optical system 10b at the beam splitter 16b. An enlarged image obtained by the enlarging optical system 10b is received by the image sensor 40 and can be observed in a large-sized monitor television 45 by an observer other than the operator.

In the above-mentioned construction, the operator places the pair of eyes coincident with the pair of ocular lens 15 of the microscope 10. In that state, the operator carries out an operation while observing the enlarged image of the diseased part by the enlarging optical systems 10a, 10b. As shown in FIG. 2, a view field range S1 of this enlarged image occupies a central portion of an entire view field range S0 of the ocular lens 15.

When the operator wants to see the image of the diseased part from a different angle, the operator manually holds the endoscope 20 and causes a distal end of the endoscope 20 to face toward the diseased part. As a consequence, the enlarged image of the diseased part obtained by the image sensor 23 of the endoscope 20 is sent to the monitor television 30 through the control unit 25. At that time, when a push button (not shown) disposed on the body 21 of the endoscope 20 is pushed, a control circuit, not shown, opens the shutter 32 in response to the actuation of the push button. As a consequence, the image displayed in the monitor television 30 is reflected by the beam splitter 13 via the lens 31 and the shutter 32 toward one of the eyes of the operator via the ocular lens 15. Consequently, the operator can observe the enlarged image of the diseased part, which is viewed from different angles, displayed in the monitor television 30 without removing the eyes from the pair of ocular lens 15.

It should be noted that the picture or image of the diseased part in the monitor television 30 observed through one of the pair of ocular lens 15 may be about the same in magnifying power as the images obtained by the enlarging optical systems 10a, 10b, or it may be higher or lower.

As shown in FIG. 2, since a view field scope S2 of the picture or image in the monitor television 30 is displaced from the view field range S1 of the enlarged image of the enlarging optical system 10a, the two images are not overlapped at all or they are not overlapped at their important portions. Accordingly, they can be observed simultaneously. In case the picture or image displayed in the monitor television 30 is found to be obstructive, the picture or image can be removed from the view field range SO of the ocular lens 15 by shutting the shutter 32.

Since the data of blood pressure, heartbeat and brain waves are also displayed in the monitor television 30, the operator can carry out an operation while taking the conditions of the patient into consideration.

In the above embodiment, the view field range S2 of the picture or image in the monitor television 30 may be overlapped with the view field range S1 of the enlarged image of the enlarging optical system 10a. In that case, another shutter is interposed between the prism 14 and the beam splitter 16a of the enlarging optical system 10a, and this shutter is shut when the picture or image in the monitor television 30 is observed.

Next other embodiments of the present invention will be described. In those embodiments, component parts corresponding to those of the first embodiment are denoted by identical reference numerals respectively and detailed description thereof is omitted.

In the embodiment of FIG. 3, a monitor television 30 is received in an ocular portion 11a of a body 11 of a microscope 10. The monitor television 30 is placed adjacent to an optical path A (more specifically, adjacent to a prism 14) of the enlarging optical system 10a and faced with an ocular lens 15. Also in this construction, an enlarged image obtained by the enlarging optical system 10a and a picture or image displayed in the monitor television 30 are mutually offset in the view field of the ocular lens 15.

Figure 4:
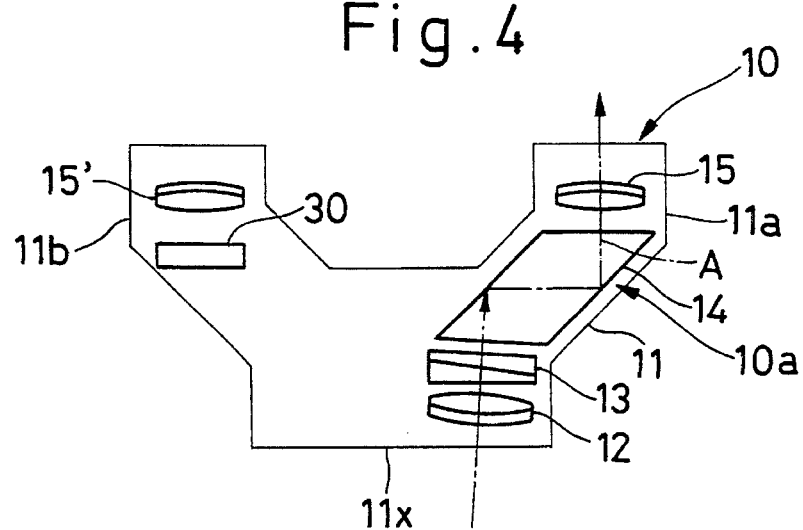
FIG. 4 is a schematic view showing an important portion of a further embodiment.

In the embodiment of FIG. 4, a microscope 10 has only a single enlarging optical system 10a. An ocular lens 15 of this enlarging optical system 10a is received in an ocular portion (one of a pair of ocular portions) 11a of a body 11, and another ocular lens 15' is received in the other ocular portion 11b. A monitor television 30 is also received in the ocular portion 11b in such a manner as to face with the ocular lens 15'. In this embodiment, the operator can observe, by one eye, an enlarged image of the diseased part obtained by the enlarging optical system 10a through the ocular lens 15 and can also observe, by the other eye, a picture or image displayed in the television monitor 30, i.e., an enlarged image of the diseased part obtained by an endoscope.

Figure 5:
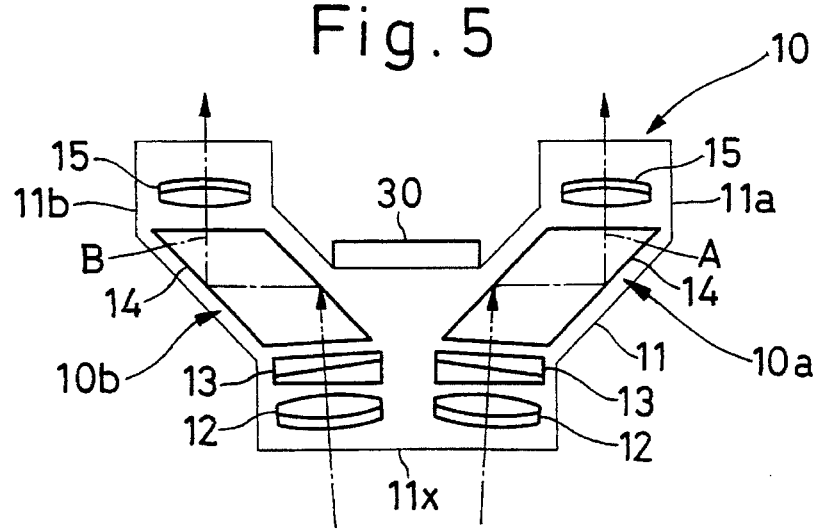
FIG. 5 is a schematic view showing an important portion of a still further embodiment.

In the embodiment of FIG. 5, a monitor television 30 is disposed on an outer surface of a base 11x of a body 11 of a microscope which outer surface is faced with the operator. The monitor television 30 is disposed between a pair of ocular portions 11a and 11b. The operator can observe an image displayed in the monitor television 30, i.e., an enlarged image of the diseased part obtained by an endoscope.

Figure 6:
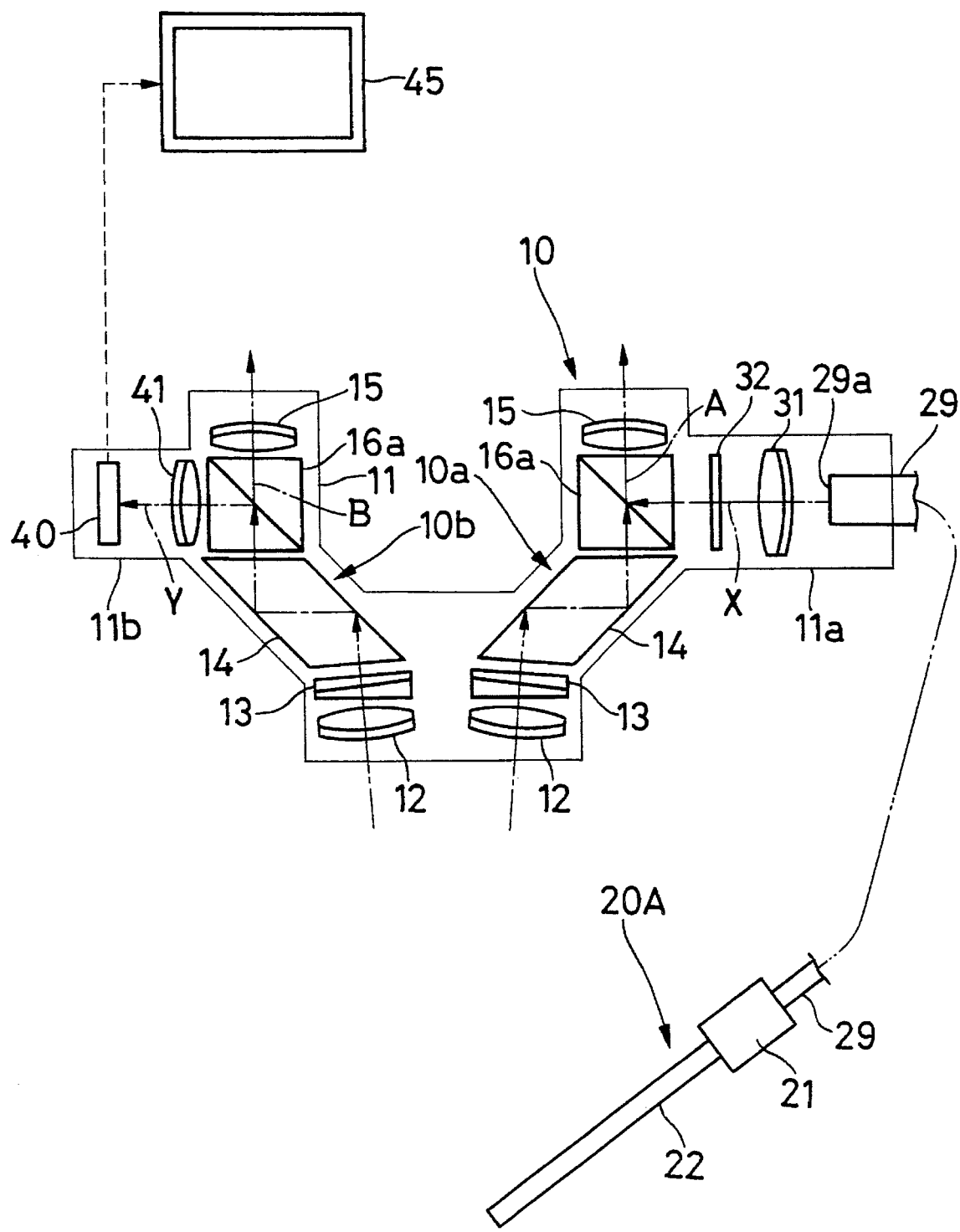
FIG. 6 is a schematic view showing a yet further embodiment.

In the embodiment of FIG. 6, an image transmission optical system of an endoscope 20A includes an optical fibers bundle 29. One end of this optical fibers bundle 29 is faced with an observing window through a lens. The optical fibers bundle 29 is allowed to extend from a body 21. The other end portion of the optical fibers bundle 29 is received in an auxiliary receiving portion 11a of the body 21 of a microscope 10. The other end face 29a of the optical fibers bundle 29 is provided as image display means. This end face 29a is intersected at right angles with an optical path X and is faced with a beam splitter 16a through a lens 31 and a shutter 32. The operator can observe not only an enlarged image of the diseased part obtained by an enlarging optical system 10a but also an image obtained by the endoscope 20A through an ocular lens 15.

The monitor television in the embodiments of FIGS. 3, 4 and 5 may be replaced by the end face of the optical fibers bundle.

What is claimed is:

1. A medical observing instrument comprising:

(a) a microscope having a body and an enlarging optical system received in said body, said enlarging optical system including an objective lens and an ocular lens to thereby obtain a first image, said enlarging optical system further including a beam splitter disposed between said objective lens and said ocular lens;

(b) an endoscope separated from said microscope; and (c) image display means connected to said endoscope and displaying a second image obtained by said endoscope, said image display means being received in said body of said microscope and placed adjacent to said beam splitter, said second image displayed in said image display means being sent to said ocular lens through said beam splitter.

2. A medical observing instrument according to claim 1, in which said endoscope includes an image sensor, and said image display means includes a monitor television connected to said image sensor.

3. A medical observing instrument according to claim 2, further comprising detection means for detecting the conditions of a patient, data from said detection means being displayed in said monitor television.

4. A medical observing instrument according to claim 1, in which said endoscope has a bundle of optical fibers for transmitting an image therethrough, said bundle of optical fibers being allowed to extend from said endoscope, an end face of an extended portion of said bundle of optical fibers being provided as said image display means.

5. The medical observing instrument according to claim 1, wherein said first image and said second image are positionally offset with each other in the view field of said ocular lens of said enlarging optical system.

6. The medical observing instrument according to claim 1, in which a shutter is disposed between said image display means and said beam splitter.

7. The medical observing instrument according to claim 1, in which said microscope further has a second enlarging optical system received in said body and disposed side by side with the first mentioned enlarging optical system, said second enlarging optical system including a second objective lens and a second ocular lens.

8. The medical observing instrument according to claim 7, in which the second enlarging optical system further includes a second beam splitter disposed between the second objective lens and the second ocular lens, an additional lens and an image sensor being placed adjacent to the second beam splitter, an image coming from the second objective lens being sent to the image sensor through the second beam splitter and said additional lens, said image sensor being in connection with a second monitor television separately situated from the microscope.

9. A medical observing instrument comprising:
(a) a microscope having a body and an enlarging optical system received in the body, said enlarging optical system including an objective lens and an ocular lens to thereby obtain a first image;
(b) an endoscope separated from the microscope; and
(c) image display means connected to the endoscope and displaying a second image obtained by the endoscope, said image display means being received in the body of the microscope and disposed adjacent to an optical path of said enlarging optical system and faced with said ocular lens, the second image displayed by said image display means being located within a view field of said ocular lens.

10. The medical observing instrument according to claim 9, in which the microscope further includes a second enlarging optical system received in the body and disposed side by side with the enlarging optical system, said second enlarging optical system including a second objective lens and a second ocular lens.

11. A medical observing instrument comprising:
(a) a microscope having a body and an enlarging optical system received in the body, said enlarging optical system including an objective lens and an ocular lens to thereby obtain a first image;
(b) an endoscope separated from the microscope; and
(c) image display means connected to the endoscope and displaying a second image obtained by the endoscope, said image display means being received in the body of the microscope;
(d) an additional ocular lens received in said body of said microscope in such a manner as to be spaced apart from said ocular lens of said enlarging optical system, said image display means being faced with said additional ocular lens.

12. A medical observing instrument comprising:
(a) a microscope having a body and a pair of enlarging optical system received in the body, each of said pair of enlarging optical system including an objective lens and an ocular lens, wherein said body of said microscope has a base portion and a pair of ocular portions projecting from said base portion, said ocular lens of said pair of enlarging optical systems being received respectively in said pair of ocular portions;
(b) an endoscope separated from said microscope; and
(c) image display means connected to said endoscope and displaying an image obtained by said endoscope, said image display means being disposed on an outer surface of said base between said pair of ocular portions.

* * * * *